(12) United States Patent
Gammons et al.

(10) Patent No.: US 7,066,949 B2
(45) Date of Patent: Jun. 27, 2006

(54) CLOSED-LOOP HEAT THERAPY BLANKET

(75) Inventors: Clifford Eugene Gammons, Loudon, TN (US); Joseph Greg Jones, Englewood, TN (US)

(73) Assignee: Adroit Medical Systems, Inc., Loudon, TN (US)

( * ) Notice: Subject to any disclaimer, the term of this patent is extended or adjusted under 35 U.S.C. 154(b) by 0 days.

(21) Appl. No.: 10/775,597

(22) Filed: Feb. 9, 2004

(65) Prior Publication Data

US 2005/0107854 A1 May 19, 2005

Related U.S. Application Data

(63) Continuation of application No. PCT/US03/36075, filed on Nov. 13, 2003.

(51) Int. Cl.
*A61F 7/00* (2006.01)
*A47C 27/00* (2006.01)

(52) U.S. Cl. ............... 607/107; 607/104; 5/423
(58) Field of Classification Search ............. 607/104, 607/107–112, 96; 5/482, 285, 423
See application file for complete search history.

(56) References Cited

U.S. PATENT DOCUMENTS

| | | | |
|---|---|---|---|
| 2,093,834 A | 9/1937 | Gaugler | |
| 4,398,535 A | 8/1983 | Guiert | |
| 4,572,188 A | 2/1986 | Augustine et al. | |
| 4,660,388 A | 4/1987 | Greene, Jr. | |
| 4,777,802 A | 10/1988 | Feher | |
| 5,106,373 A | 4/1992 | Augustine et al. | |
| 5,184,612 A | 2/1993 | Augustine | |
| 5,300,102 A | 4/1994 | Augustine et al. | |
| 5,304,213 A | 4/1994 | Berke et al. | |
| 5,324,320 A | 6/1994 | Augustine et al. | |
| 5,336,250 A | 8/1994 | Augustine | |
| 5,350,417 A | 9/1994 | Augustine | |
| 5,405,370 A * | 4/1995 | Irani | 607/104 |
| 5,405,371 A | 4/1995 | Augustine et al. | |
| 5,928,274 A | 7/1999 | Augustine | |
| 5,989,285 A * | 11/1999 | DeVilbiss et al. | 607/107 |
| 6,168,612 B1 | 1/2001 | Augustine et al. | |
| 6,493,889 B1 * | 12/2002 | Kocurek | 5/423 |
| 6,519,964 B1 * | 2/2003 | Bieberich | 62/259.3 |
| 6,537,307 B1 * | 3/2003 | Augustine et al. | 607/107 |
| 6,699,270 B1 | 3/2004 | Gammons et al. | |
| 2003/0208251 A1 * | 11/2003 | Papay et al. | 607/107 |

* cited by examiner

*Primary Examiner*—Roy D. Gibson
(74) *Attorney, Agent, or Firm*—Pitts & Brittian, PC

(57) ABSTRACT

A closed loop heat therapy blanket provided for warming a patient to prevent or treat hypothermia. The closed loop heat therapy blanket includes first and second sheets secured to each other such as to define a supply manifold, at least one supply duct, a return manifold and a return duct. The first sheet defines a supply inlet opening into the supply manifold and a return outlet opening from the return duct. Heated air is introduced into the supply manifold and travels through to the return outlet and through an outlet hose. As the heated air travels through the blanket, a portion is communicated through the second sheet and toward the patient. A heat source is provided for collecting and heating ambient air, and for collecting preheated air from the outlet hose. In one embodiment, a humidifier is provided for controlling the moisture in the air being directed toward the patient.

10 Claims, 4 Drawing Sheets

CLOSED-LOOP HEAT THERAPY BLANKET

CROSS-REFERENCE TO RELATED APPLICATIONS

This application is a continuation of, and claims the benefit of, International Application No. PCT/US03/36075, filed Nov. 13, 2003.

STATEMENT REGARDING FEDERALLY SPONSORED RESEARCH OR DEVELOPMENT

Not Applicable

BACKGROUND OF THE INVENTION

1. Field of Invention

This invention pertains to convective heat therapy blankets. More specifically, the present invention relates to a heat therapy blanket wherein heated air not directed to the patient is recirculated through the blanket to recapture heat, thereby reducing heat emitted into the surrounding environment and reducing the required capacity of the associated heater.

2. Description of the Related Art

In the field of patient warming, it is well known that hypothermia is of concern. Hypothermia has been defined as a condition of subnormal body temperature which presents serious consequences to the patient. It has been shown that a large percentage of surgical patients develop hypothermia. The hypothermic condition is brought on by many factors including anesthesia, the air conditioning of the operating room, and the infusion of cold blood, I-V solutions, or irrigating fluids. Outside an operating room, hypothermia can occur when an individual has had prolonged exposure to a hostile environment such as freezing rain, snow or bitter cold.

Regardless of the cause of hypothermia, the individual initially experiences extreme discomfort which can quickly lead to a life threatening situation. It is known that one suffering from hypothermia must be attended to quickly in order to avoid irreversible body temperature drop or even death. Simply wrapping a person suffering from hypothermia in a blanket is a solution which can provide some relief, the blanket helping to retain body heat. This results in a gradual warming of the body. However, this method is not always sufficient to overcome hypothermia. The ability of the body to produce sufficient heat in sufficient time may not be possible or feasible in certain situations. Additionally, use of a blanket during or after an operation in a hospital can be cumbersome. It may be difficult to fully cover the patient's body due to intravenous tubing and other life supporting equipment which physically hinders placement of the blanket.

Another method used for heat therapy is an inflatable blanket used to direct heated air to a patient. Typically, these are used for surgical patients to maintain body temperatures while undergoing surgical or other procedures. A concern that arises in the use of such is the direct contact of heated air with an open wound or other skin conditions. This is especially of concern when the heated air is contaminated.

Various devices have been developed for heat therapy. Typical of the art are those devices disclosed in the following U.S. Patents:

| U. S. Pat. No. | Inventor(s) | Issue Date |
| --- | --- | --- |
| 2,093,834 | R. S. Gaugler | Sep. 21, 1937 |
| 4,572,188 | S. D. Augustine et al. | Feb. 25, 1986 |
| 4,660,388 | G. J. Greene, Jr. | Apr. 28, 1987 |
| 4,777,802 | S. Feher | Oct. 18, 1988 |
| 5,106,373 | S. D. Augustine et al. | Apr. 21, 1992 |
| 5,184,612 | S. D. Augustine | Feb. 9, 1993 |
| 5,300,102 | S. D. Augustine et al. | Apr. 5, 1994 |
| 5,304,213 | L. D. Berke et al. | Apr. 19, 1994 |
| 5,324,320 | S. D. Augustine et al. | Jun. 28, 1994 |
| 5,336,250 | S. D. Augustine | Aug. 9, 1994 |
| 5,350,417 | S. D. Augustine | Sep. 27, 1994 |
| 5,405,371 | S. D. Augustine et al. | Apr. 11, 1995 |

Of these patents, the '834 patent issued to Gaugler discloses a refrigerating apparatus including an air blanket and a heating or cooling unit. The air blanket is fabricated from three layers of material. The lower layer is provided as a sheet to be placed over the user. Between the first and second layers is defined a plurality of air ducts through which the air travels. The lower layer is air-permeable such to direct the air to the user. The upper layer is provided to limit the bulging of the second layer when air is injected through the air ducts. In one embodiment, the air blanket defines a U-shaped return duct between the second and upper layers blanket. The '834 device is also described as having an evaporator for use when cooling the user and a humidifier when heating the user, the evaporator and humidifier each being provided for controlling the humidity of the air being directed toward the user.

The remaining patents disclose various air blankets for directing temperature controlled air toward a person situated under the blanket. Generally, these devices include a bottom layer constructed to be air-permeable and a top layer fabricated from an air-impermeable material. The bottom layer may be fabricated from an air-impermeable material and provided with openings for the passage of air, or may be fabricated from an air-permeable material. Each blanket defines a series of baffles through which the air travels before being directed through the bottom layer.

With these devices, air not directed to the person is forced into the surrounding environment in which the blanket is utilized. In an operating room, the exhaust of heated air into the room is adverse to the medical professionals who are trying to remain cool. The need to keep the patient warm takes precedent over the need to keep the medical professionals cool. However, an ideal situation provides for the patient to be warmed without substantially effecting the temperature of the immediate surroundings.

Illustrated generically in FIGS. 1 and 2 is one embodiment similar to the above devices 10P. A lower sheet 24P is dimensioned to cover the patient and drape over the sides of the bed (not shown). An air-impermeable upper sheet 12P is fixed to the lower sheet 24P. Baffles 58P are defined between the upper and lower sheets 12P,24P in a conventional manner such as by sonic welding, sewing or the like. The lower sheet 24P may be fabricated from either an air-impermeable or an air-permeable material. In the instance of an air-impermeable lower sheet, openings 28P are defined in the lower sheet 24P in order to direct air onto the patient. In the embodiment where the lower sheet 24P is air-permeable, the air is directed through the material to the patient without requiring openings 28P.

Other devices are disclosed in European Patent No. 716,746 issued to R. V. Lee on Oct. 13, 1954. One embodiment of the '746 device disclosed by Lee is an air conditioning cover for use on beds. The device includes an air blanket fabricated from upper and lower sheets quilted together at intervals to accomplish air circulation between the sheets. An opening is defined at one end of the upper sheet to receive an inlet duct. The upper and lower sheets are fabricated from an air-permeable material such that air directed through the inlet duct and between the upper and lower sheets is then directed through the upper and lower sheets.

BRIEF SUMMARY OF THE INVENTION

The present invention is a closed loop heat therapy blanket provided for warming a patient to prevent or treat hypothermia. The closed loop heat therapy blanket is provided for communicating heated air to a patient in a manner that releases minimal heated air to the surroundings, thus allowing the surroundings to remain more comfortable to others such as medical professionals tending to the patient. Heated air that is not directed specifically at the patient is recirculated, thereby reducing the required heating capacity of an associated heat source.

The closed loop heat therapy blanket is primarily comprised of a first or upper sheet and a second or lower sheet secured to each other in a conventional manner at a plurality of securement regions. A first securement region is defined about the perimeter of the first sheet. A substantially U-shaped second securement region is positioned a selected distance inside the first securement region in order to define a return duct along each side and at a proximal end of the first sheet. At least one third securement region is defined inside the second securement region to define a return manifold at the distal end of the first sheet, a plurality of supply ducts along the length of the first sheet, and a supply manifold at the proximal end of the first sheet and inside the second securement region.

The first sheet defines a supply inlet opening into the supply manifold and to which a supply hose is releasably connectable. The first sheet further defines a return outlet opening from the return duct and to which a return hose is releasably connectable.

Heated air is introduced into the supply manifold via the supply hose. The heated air then travels through the supply ducts and toward the return manifold. From the return manifold, the heated air continues through the return duct and out through the return outlet and through the outlet hose. The air forced into the blanket is under pressure such that as it travels through each of the supply manifold, the supply ducts, the return manifold, and the return ducts, a portion of the heated air is communicated through the second sheet and onto and around the patient.

The second sheet extends in all directions from the first sheet in order to define a skirt. The skirt is provided for draping over the patient and extending at least to the surface of the bed, thus defining a discrete volume of air under the blanket and surrounding the patient that is to be heated. The skirt thus retains a substantial portion of the heated air communicated toward the patient.

The first sheet is fabricated from an air-impermeable material in order to prevent heated air from escaping to the surrounding environment. The second sheet is fabricated from an air-permeable material in order to allow heated air to be communicated to the patient. In the alternative, the second sheet is fabricated from an air-impermeable material and is provided with openings for the passage of heated.

A heat source is provided for collecting ambient air, heating it, and directing it toward the patient through the second or lower sheet of blanket. The heated air is then communicated through the supply hose to the blanket. The heated air then travels through the blanket and at least a portion of the heated air is communicated out of the blanket and toward the patient. The heat source also serves to intake supplemental air to mix with the preheated air coming from the return hose in order to supply the blanket with sufficient pressure to force the heated air through the second sheet and toward the patient.

A humidifier is provided for controlling the moisture in the air being directed toward the patient. In order to prevent the moisture from being exhausted into the surroundings, both the first and second sheets are fabricated from materials that serve as moisture barriers.

BRIEF DESCRIPTION OF THE SEVERAL VIEWS OF THE DRAWINGS

The above-mentioned features of the invention will become more clearly understood from the following detailed description of the invention read together with the drawings in which.

DETAILED DESCRIPTION OF THE INVENTION

A closed loop heat therapy blanket is provided for warming a patient to prevent or treat hypothermia. The closed loop heat therapy blanket is illustrated generally at 10 in the figures and is provided for communicating heated air to a patient in a manner that releases minimal heated air to the surroundings, thus allowing the surroundings to remain more comfortable to others such as medical professionals tending to the patient. Heated air that is not directed specifically at the patient is recirculated, thereby reducing the required heating capacity of an associated heat source 68. Heat is directed toward the patient through the closed loop heat therapy blanket 10, but not as heated air, thereby preventing any contaminants that may be in the heated air from reaching the patient and infecting any open wounds or exacerbating any skin conditions.

Figure 1:
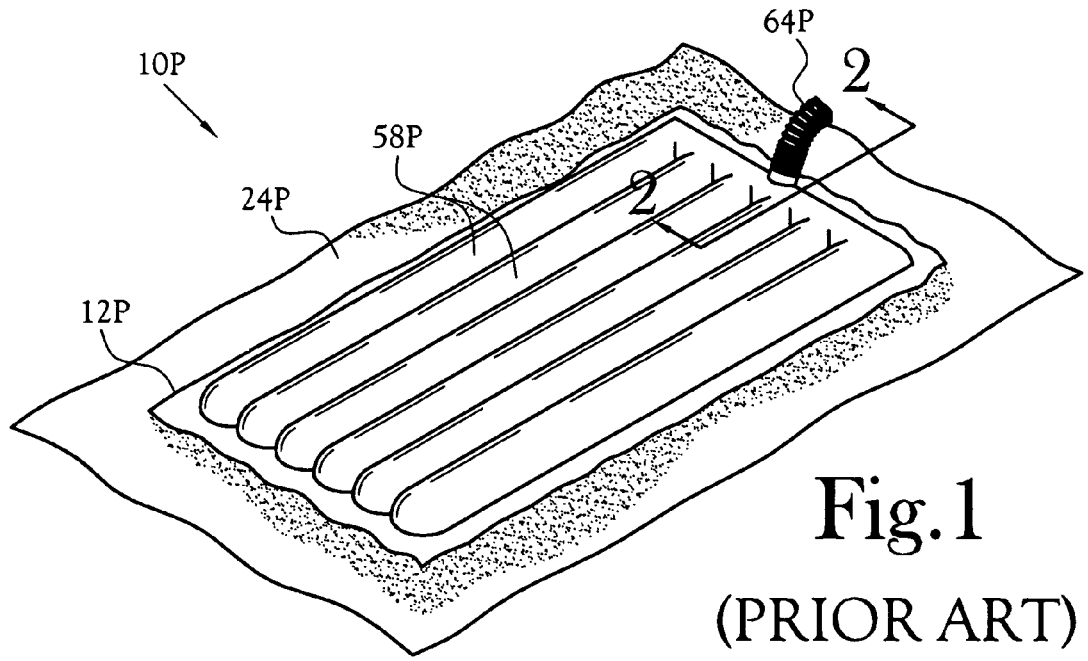
FIG. 1 is a perspective illustration of a prior art thermal heating blanket.
Figure 2:
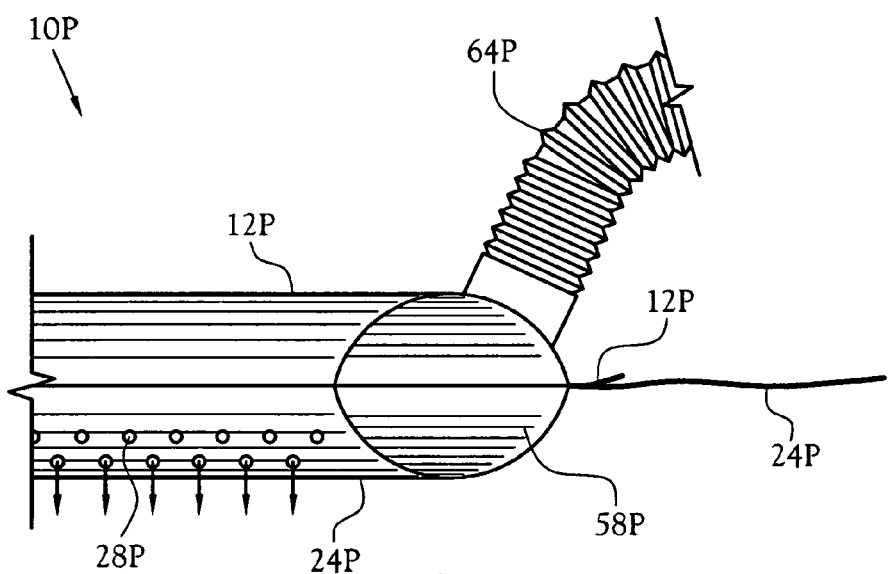
FIG. 2 is an elevation view, in section, of the prior art thermal heating blanket taken at 2—2 of FIG. 1.
Figure 3:
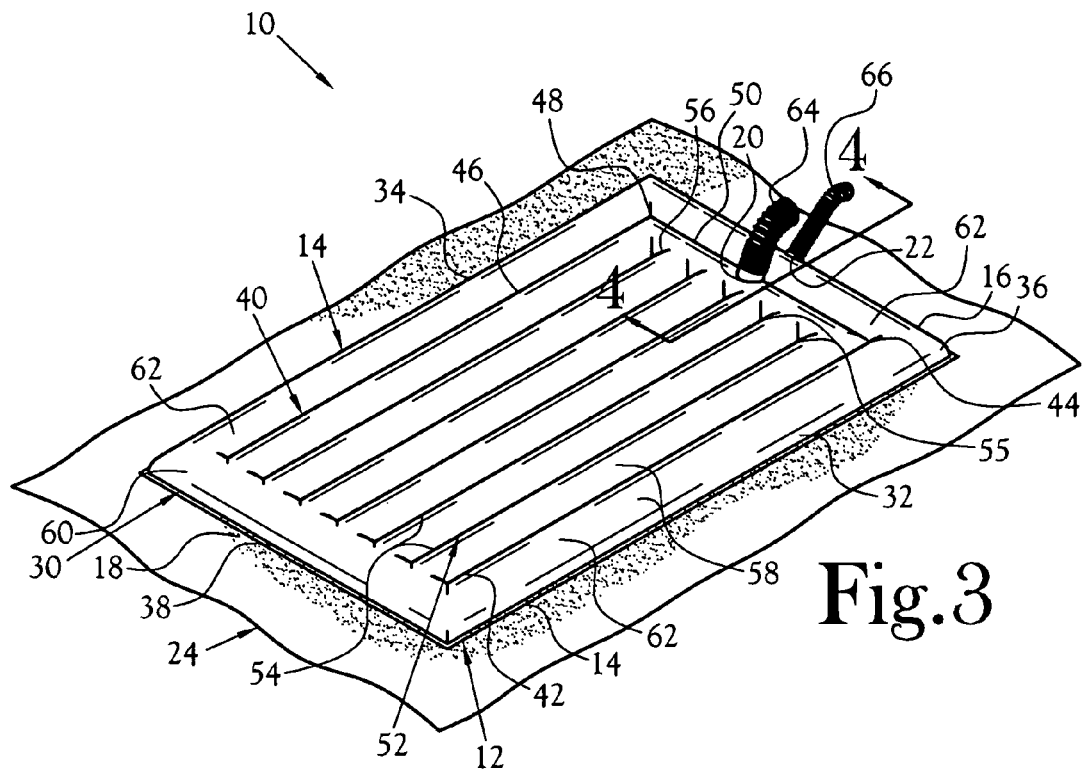
FIG. 3 is a perspective illustration of a recirculating thermal heating blanket constructed in accordance with several features of the present invention.

As best illustrated in FIG. 3, the closed loop heat therapy blanket 10, or blanket 10, is primarily comprised of a first or upper sheet 12 and a second or lower sheet 24. The first and second sheets 12,24 are secured to each other in a conventional manner such as by sonic welding, gluing or sewing. A plurality of securement regions are defined, in which the first and second sheets 12,24 are secured one to the other as described. In the illustrated embodiment, first, second and third securement regions 30,40 and 52 are defined.

The first securement region 30 is defined about a perimeter of the first sheet 12 and includes first and second longitudinal regions 32,34 disposed along opposing sides 14 of the first sheet 12 and first and second lateral regions 36,38 disposed at a proximal end 16 and a distal end 18 of the first sheet 12, respectively. Each of the first and second longitudinal regions 32,34 and the first and second lateral regions 36,38 are connected in an end-to-end fashion.

The second securement region 40 includes third and fourth longitudinal regions 42,46 and a third lateral region 50. The third and fourth longitudinal regions 42,46 are disposed between the first and second longitudinal regions 32,34 of the first securement region 30. The third lateral region 50 is positioned in end-to-end fashion at a proximal end 44,48 of the third and fourth longitudinal regions 42,46, respectively, such that the second securement region 40 defines a substantially U-shaped configuration. A return duct 62 is defined between the first and third longitudinal regions 32,42, the second and fourth longitudinal regions 34,46, and the first and third lateral regions 36,50.

A third securement region 52 includes at least one fifth longitudinal region 54 defined between said third and fourth longitudinal regions 42,46 defined by the second securement region 40. A supply manifold 56 is defined between the third lateral region 50 of the second securement region 40 and a proximal end 55 of each fifth longitudinal region 54. At least one supply duct 58 is defined between successive pairs of the third, fourth and fifth longitudinal regions 42,46,54. A return manifold 60 is defined between a distal end 45,49,57 of the third, fourth and fifth longitudinal regions 42,46,54, respectively, and the second lateral region 38.

The first sheet 12 defines a supply inlet 20 to which a supply hose 64 is releasably connectable. The supply inlet 20 opens into the supply manifold 56. The first sheet 12 further defines a return outlet 22 to which a return hose 66 is releasably connectable. The return outlet 22 opens into the return duct 62.

Following the flow of heated air, the air is introduced into the supply manifold 56 via the supply hose 64. The heated air then travels through the supply ducts 58 and toward the return manifold 60. From the return manifold 60, the heated air continues through the return duct 62 and out through the return outlet 22 and through the return hose 66. Because the air forced into the blanket 10 is under pressure, as it travels through each of the supply manifold 56, the supply ducts 58, the return manifold 60, and the return ducts 62, a portion of the heated air is communicated through the second sheet 24 and onto and around the patient.

The second sheet 24 extends in all directions from the first sheet 12 in order to define a skirt 26. The skirt 26 is provided for draping over the patient and extending at least to the surface of the bed, thus defining a discrete volume of air under the blanket 10 and surrounding the patient that is to be heated. The skirt 26 thus retains a substantial portion of the heated air communicated toward the patient.

Figure 4:
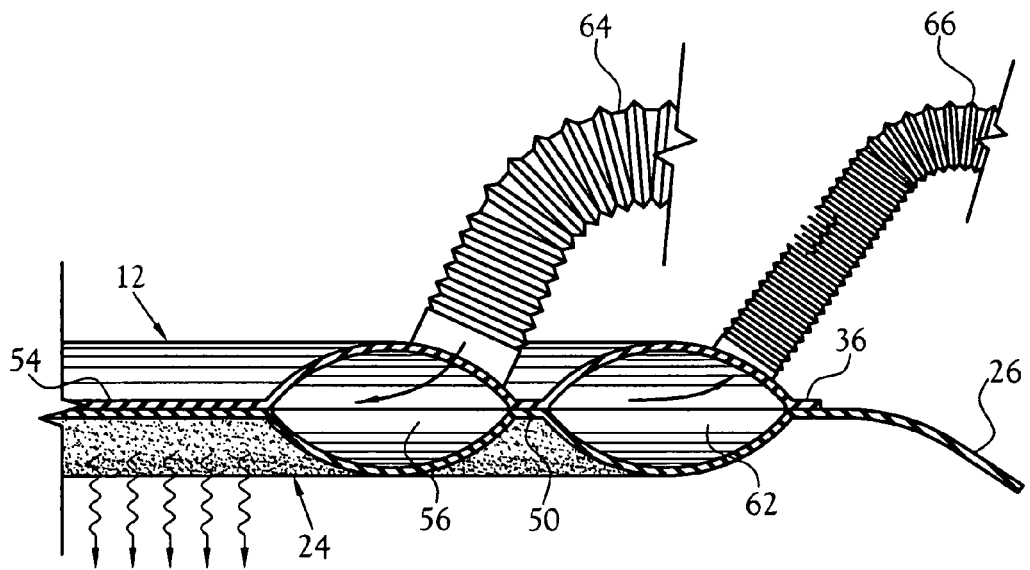
FIG. 4 is an elevation view, in section, of the recirculating thermal heating blanket taken at 4—4 of FIG. 3.
Figure 4A:
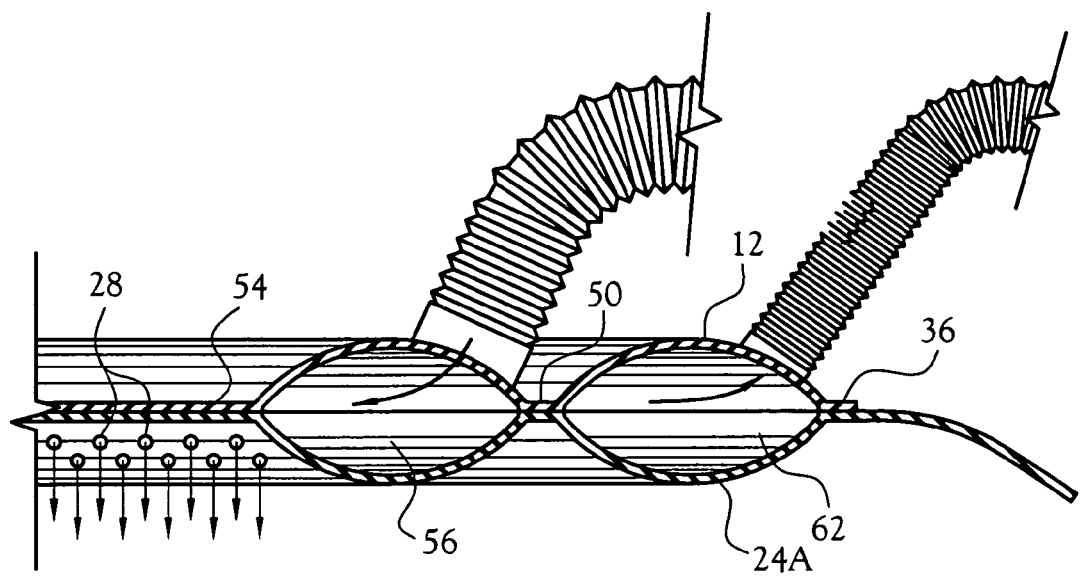
FIG. 4A is an elevation view, in section, of an alternate embodiment of the recirculating thermal heating blanket taken at 4—4 of FIG. 3.

FIGS. 4 and 4A better illustrate that the first sheet 12 is fabricated from an air-impermeable material in order to prevent heated air from escaping to the surrounding environment. It will be understood by those skilled in the art that various conventional materials provide air-impermeability sufficient for the purposes of the present invention. In the embodiment illustrated in FIG. 4, the second sheet 24 is fabricated from an air-permeable material in order to allow heated air to be communicated to the patient. In the alternative illustrated in FIG. 4A, the second sheet 24A is fabricated from an air-impermeable material and is provided with openings 28 for communicating the heated air toward the patient.

Figure 5:
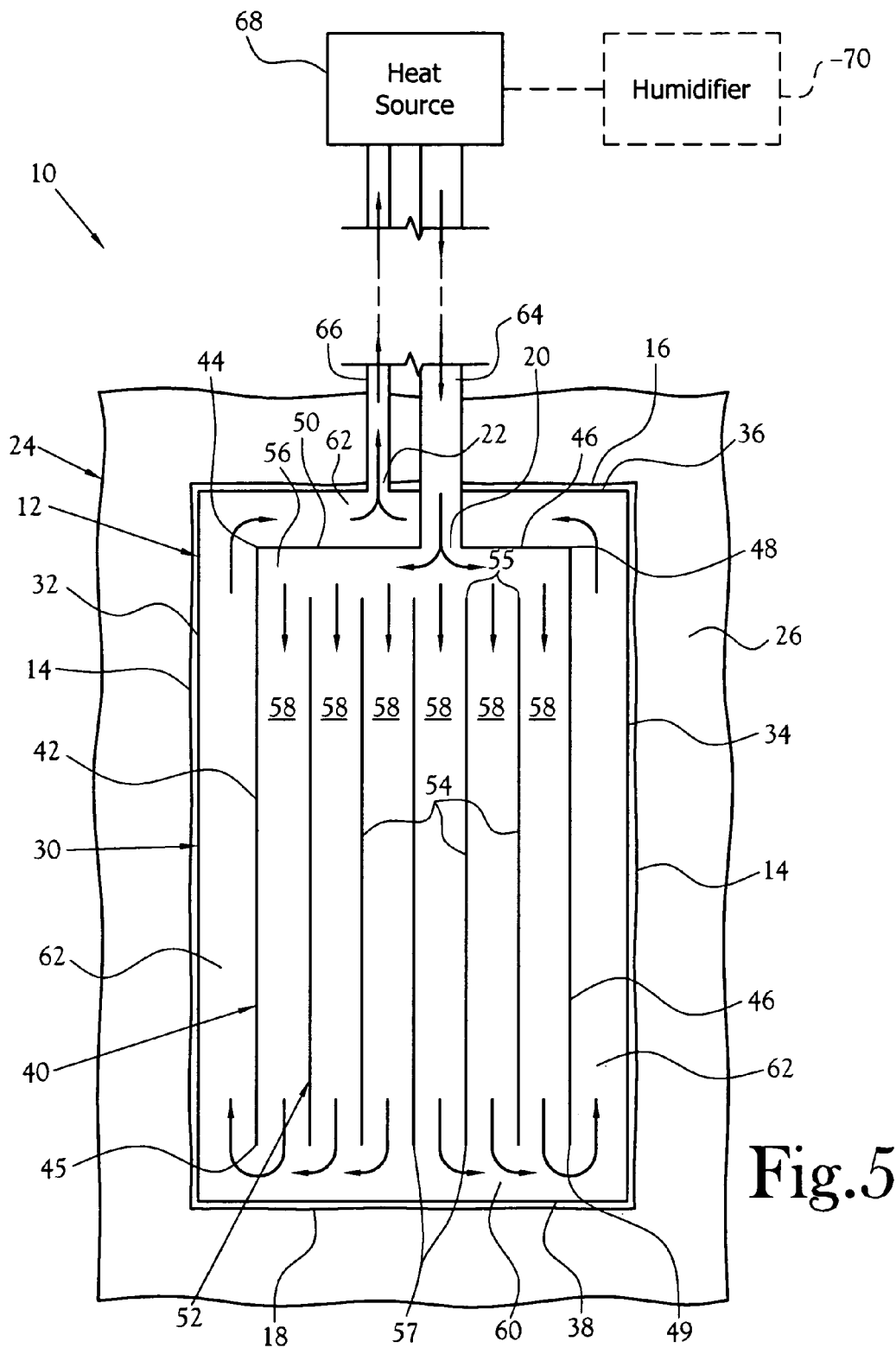
FIG. 5 is a schematic illustration of the recirculating thermal blanket of FIG. 3 shown in a closed loop circuit with a heat source and, in the alternative, with a humidifier.

FIG. 5 illustrates schematically the closed loop in which the blanket 10 is deployed. A heat source 68 is provided for collecting ambient air, heating it, and directing it toward the patient through the second or lower sheet 24 of blanket 10. The heated air is then communicated through the supply hose 64 to the blanket 10. The heated air then travels through the blanket 10 as described above. Since at least a portion of the heated air is communicated out of the blanket 10 and toward the patient, the heat source 68 also serves to intake supplemental air to mix with the preheated air coming from the return hose 66 in order to supply the blanket 10 with sufficient pressure to force the heated air through the second sheet 24 and toward the patient.

Illustrated in phantom is a humidifier 70 for controlling the moisture in the air being directed toward the patient. In a conventional system, introducing moisture into the air stream is risky in view of airborne pathogens. However, in the present invention, an elevated humidity helps to increase the heat conductivity of the air. In order to prevent the moisture from being exhausted into the surroundings, both the first and second sheets 12,24 are fabricated from materials that serve as moisture barriers.

From the foregoing description, it will be recognized by those skilled in the art that a closed loop heat therapy blanket offering advantages over the prior art has been provided. Namely, as compared to conventional convection heating apparatuses in which all of the heated air generated by the heat source is evacuated from the thermal blanket, only that air necessary to heat the patient and the volume of air under the blanket is communicated from the blanket. The remaining heated air is communicated back to be mixed with supplemental air to be heated. Because a portion of the air is preheated, the heating requirements of the heat source are reduced. Further, because excess heated air is not being introduced into the surroundings of the blanket, those working in the surroundings are not inconvenienced by heat.

While the present invention has been illustrated by description of several embodiments and while the illustrative embodiments have been described in considerable detail, it is not the intention of the applicant to restrict or in any way limit the scope of the appended claims to such detail. Additional advantages and modifications will readily appear to those skilled in the art. The invention in its broader aspects is therefore not limited to the specific details, representative apparatus and methods, and illustrative examples shown and described. Accordingly, departures may be made from such details without departing from the spirit or scope of the general inventive concept.

Having thus described the aforementioned invention, we claim:

1. A heat therapy blanket for communicating heated air toward a patient to prevent or treat hypothermia, said heat therapy blanket comprising:
   a first sheet defining first and second sides and proximal and distal ends;
   a second sheet secured to said first sheet at a plurality of securement regions, said plurality of securement regions being configured to define a supply manifold at said proximal end extending between said first and second sides, at least one first supply duct extending between said proximal and distal ends along said first side, at least one second supply duct extending between said proximal and distal ends along said second side, a return manifold at said distal end extending between said first and second sides, and at least one return duct extending from said return manifold and terminating proximate said supply manifold and disposed between said first and second supply ducts, said second sheet extending away from each of said first and second sides and said proximal and distal end of said first sheet to define a skirt for draping over the patient to define a discrete volume of air under said heat therapy blanket and surrounding the patient whereby a substantial portion of the heated air communicated toward the patient is contained in said discrete volume of air;

a supply inlet carried by said first sheet and adapted to releasably connect a supply hose to said supply manifold;

a return outlet carried by said first sheet and adapted to releasably connect a return hose to said return duct, whereby heated air is introduced into said supply manifold via the supply hose, through said at least one supply duct, through said return manifold, through said at least one return duct, and through said outlet hose; and a heat source for collecting, heating and directing ambient air toward the patient through said second sheet.

2. The heat therapy blanket of claim 1 wherein said plurality of securement regions includes:

a first securement region being defined about a perimeter of said first sheet, said first securement region including first and second longitudinal regions disposed along opposing sides of said first sheet and first and second lateral regions disposed at a proximal end and a distal end of said first sheet, respectively, each of said longitudinal regions and said lateral regions being connected in an end-to-end fashion;

a second securement region including third and fourth longitudinal regions and a third lateral region, said third and fourth longitudinal regions being disposed between said first and second longitudinal regions of said first securement region, said third lateral region being positioned in end-to-end fashion at a proximal end of said third and fourth longitudinal regions, said return duct being defined between said first and third longitudinal regions, said second and fourth longitudinal regions, and said first and third lateral regions; and a third securement region including at least one fifth longitudinal region defined between said third and fourth longitudinal regions defined by said second securement region, said supply manifold being defined between said third lateral region of said second securement region and a proximal end of said at least one fifth longitudinal region, said at least one supply duct being defined between successive pairs of said third, fourth and fifth longitudinal regions, and said return manifold being defined between a distal end of said third, fourth and fifth longitudinal regions and said second lateral region.

3. The heat therapy blanket of claim 1 further comprising a humidifier in communication with said heat source for controlling the moisture in air being heated and directed through said second sheet.

4. The heat therapy blanket of claim 1 wherein said first sheet is fabricated from an air-impermeable material whereby heated air is substantially prevented from escaping to the surrounding environment.

5. The heat therapy blanket of claim 1 wherein said second sheet is fabricated from an air-impermeable material, said second sheet defining a plurality of openings for communicating heated air toward the patient.

6. The heat therapy blanket of claim 1 wherein said second sheet is fabricated from an air-permeable material whereby heated air is communicated through said second sheet toward the patient.

7. A heat therapy blanket for communicating heated air toward a patient to prevent or treat hypothermia, said heat therapy blanket comprising:

a first sheet defining first and second sides and proximal and distal ends, said first sheet being fabricated from an air-impermeable material whereby heated air is substantially prevented from escaping to the surrounding environment;

a second sheet secured to said first sheet at a plurality of securement regions, said plurality of securement regions being configured to define a supply manifold at said proximal end extending between said first and second sides, at least one first supply duct extending between said proximal and distal ends along said first side, at least one second supply duct extending between said proximal and distal ends along said second side, a return manifold at said distal end extending between said first and second sides, and at least one return duct extending from said return manifold and terminating proximate said supply manifold and disposed between said first and second supply ducts, said second sheet extending away from each of said first and second sides and said proximal and distal end of said first sheet to define a skirt for draping over the patient to define a discrete volume of air under said heat therapy blanket and surrounding the patient whereby a substantial portion of the heated air communicated toward the patient is contained in said discrete volume of air, said plurality of securement regions including:

a first securement region being defined about a perimeter of said first sheet, said first securement region including first and second longitudinal regions disposed along opposing sides of said first sheet and first and second lateral regions disposed at a proximal end and a distal end of said first sheet, respectively, each of said longitudinal regions and said lateral regions being connected in an end-to-end fashion;

a second securement region including third and fourth longitudinal regions and a third lateral region, said third and fourth longitudinal regions being disposed between said first and second longitudinal regions of said first securement region, said third lateral region being positioned in end-to-end fashion at a proximal end of said third and fourth longitudinal regions, said return duct being defined between said first and third longitudinal regions, said second and fourth longitudinal regions, and said first and third lateral regions; and a third securement region including at least one fifth longitudinal region defined between said third and fourth longitudinal regions defined by said second securement region, said supply manifold being defined between said third lateral region of said second securement region and a proximal end of said at least one fifth longitudinal region, said at least one supply duct being defined between successive pairs of said third, fourth and fifth longitudinal regions, and said return manifold being defined between a distal end of said third, fourth and fifth longitudinal regions and said second lateral region;

a supply inlet carried by said first sheet and adapted to releasably connect a supply hose to said supply manifold;

a return outlet carried by said first sheet and adapted to releasably connect a return hose to said return duct, whereby heated air is introduced into said supply manifold via the supply hose, through said at least one supply duct, through said return manifold, through said at least one return duct, and through said outlet hose; and a heat source for collecting, heating and directing ambient air toward the patient through said second sheet.

8. The heat therapy blanket of claim 7 further comprising a humidifier in communication with said heat source for controlling the moisture in air being heated and directed through said second sheet.

9. The heat therapy blanket of claim 7 wherein said second sheet is fabricated from an air-impermeable material, said second sheet defining a plurality of openings for communicating heated air toward the patient.

10. The heat therapy blanket of claim 7 wherein said second sheet is fabricated from an air-permeable material whereby heated air is communicated through said second sheet toward the patient.

* * * * *